United States Patent
Dai et al.

(10) Patent No.: US 11,781,108 B2
(45) Date of Patent: *Oct. 10, 2023

(54) METHOD FOR PRODUCING NERVOUS SYSTEM CELLS

(71) Applicants: KYOTO PREFECTURAL PUBLIC UNIVERSITY CORPORATION, Kyoto (JP); KATAOKA CORPORATION, Kyoto (JP)

(72) Inventors: Ping Dai, Kyoto (JP); Tetsuro Takamatsu, Kyoto (JP)

(73) Assignees: KYOTO PREFECTURAL PUBLIC UNIVERSITY CORPORATION, Kyoto (JP); KATAOKA CORPORATION, Kyoto (JP)

(*) Notice: Subject to any disclaimer, the term of this patent is extended or adjusted under 35 U.S.C. 154(b) by 232 days.

This patent is subject to a terminal disclaimer.

(21) Appl. No.: 15/544,604

(22) PCT Filed: Jan. 18, 2016

(86) PCT No.: PCT/JP2016/051302
§ 371 (c)(1),
(2) Date: Jul. 19, 2017

(87) PCT Pub. No.: WO2016/117510
PCT Pub. Date: Jul. 28, 2016

(65) Prior Publication Data
US 2018/0010092 A1    Jan. 11, 2018

(30) Foreign Application Priority Data

Jan. 20, 2015   (JP) .................................. 2015-008870
Mar. 27, 2015   (WO) .................. PCT/JP2015/059651

(51) Int. Cl.
*C12N 5/0793* (2010.01)
*A61K 35/30* (2015.01)
*A61K 35/33* (2015.01)

(52) U.S. Cl.
CPC ............ *C12N 5/0619* (2013.01); *A61K 35/30* (2013.01); *A61K 35/33* (2013.01); *C12N 2501/01* (2013.01); *C12N 2501/15* (2013.01); *C12N 2501/155* (2013.01); *C12N 2501/405* (2013.01); *C12N 2501/727* (2013.01); *C12N 2506/1307* (2013.01)

(58) Field of Classification Search
None
See application file for complete search history.

(56) References Cited

U.S. PATENT DOCUMENTS

| | | |
|---|---|---|
| 2010/0167300 A1 | 7/2010 | Esmaeli-Azad |
| 2010/0233804 A1 | 9/2010 | Zhou et al. |
| 2010/0267141 A1 | 10/2010 | Shi et al. |
| 2011/0110899 A1 | 5/2011 | Shi et al. |
| 2012/0214234 A1* | 8/2012 | Takamatsu ........... C12N 5/0696 435/375 |
| 2013/0273536 A1 | 10/2013 | Shi et al. |
| 2015/0225700 A1 | 8/2015 | Esmaeli-Azad |
| 2016/0068806 A1* | 3/2016 | Ashton ................ C12N 5/0619 435/368 |
| 2017/0159012 A1* | 6/2017 | Chambers ............ C12N 5/0619 |

FOREIGN PATENT DOCUMENTS

| | | |
|---|---|---|
| JP | 2011-517560 | 6/2011 |
| WO | 2009/117439 | 9/2009 |
| WO | 2010/068955 | 6/2010 |
| WO | WO-2014104409 A1 * | 7/2014 ........... C12N 5/0623 |

OTHER PUBLICATIONS

Zosen et al (Ross Fiziol Zh Im M Sechenova 100: 1431-1442, 2014) abstract only.*
Dai et al (J Clin Biochem Nut 56: 166-170, published online Apr. 1, 2015).*
Li et al (Cell Stem Cell 17: 195-203, Aug. 2015).*
Sun et al (Nat Commun 5: 1-10, published online Jun. 2014).*
Velasco et al (Stem Cells 32: 2811-2817, 2014).*
Lepski et al (Front Cell Neurosc 7: 1-11, 2013).*
Raciti et al (Mol Cell Neurosc 57: 42-53, 2013).*
Deng et al (BBRC 282: 148-152, 2001).*
Lu et al (J Neurosc Res 77: 174-191, 2004).*
Lairson et al (Ann Rev Pharmacol Toxicol 53: 107-125, 2013).*
International Search Report dated Mar. 8, 2016 in International Application No. PCT/JP2016/051302.
International Preliminary Report on Patentability dated Jul. 25, 2017 in International Application No. PCT/JP2016/051302.
Thoma E.C., et al., "Chemical Conversion of Human Fibroblasts into Functional Schwann Cells", Stem Cell Reports, Oct. 2014, vol. 3, p. 539-547, ISSN 2213-6711, particularly, Summary, Introduction.
Jikken Igaku (Experimental medicine), 2012, vol. 30, pp. 189-196.
Lin Cheng, et al., "Generation of neural progenitor cells by chemical cocktails and hypoxia", Cell Research (2014) 24:665-679.
Office Action dated Mar. 9, 2018 issued in corresponding Japanese patent application No. 2016-570628 with Machine Translation.

(Continued)

*Primary Examiner* — Daniel E Kolker
*Assistant Examiner* — Aditi Dutt
(74) *Attorney, Agent, or Firm* — Wenderoth, Lind & Ponack, L.L.P.

(57) ABSTRACT

The present invention provides a method with which it is possible to directly induce nervous system cells efficiently and in a short amount of time. Because the method is easy to scale up and is not affected by the characteristics or background of the somatic cells used as material, the method enables the stable supply of nervous system cells. The nervous system cells obtained by the method are useful in various fields of research and healthcare.

7 Claims, 1 Drawing Sheet

(56) References Cited

OTHER PUBLICATIONS

Office Action dated Mar. 16, 2020 in corresponding Chinese Patent application No. 201680017236.3, with Machine Translation.

* cited by examiner

[Fig.1]
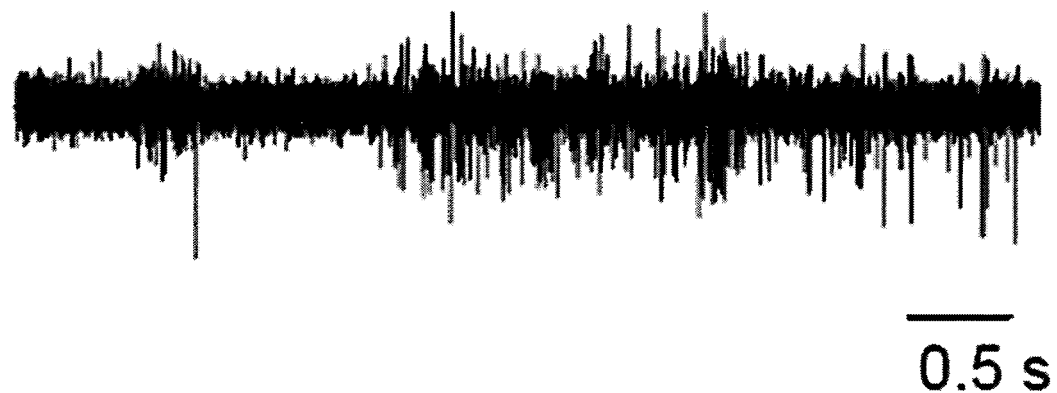
[Fig.2]
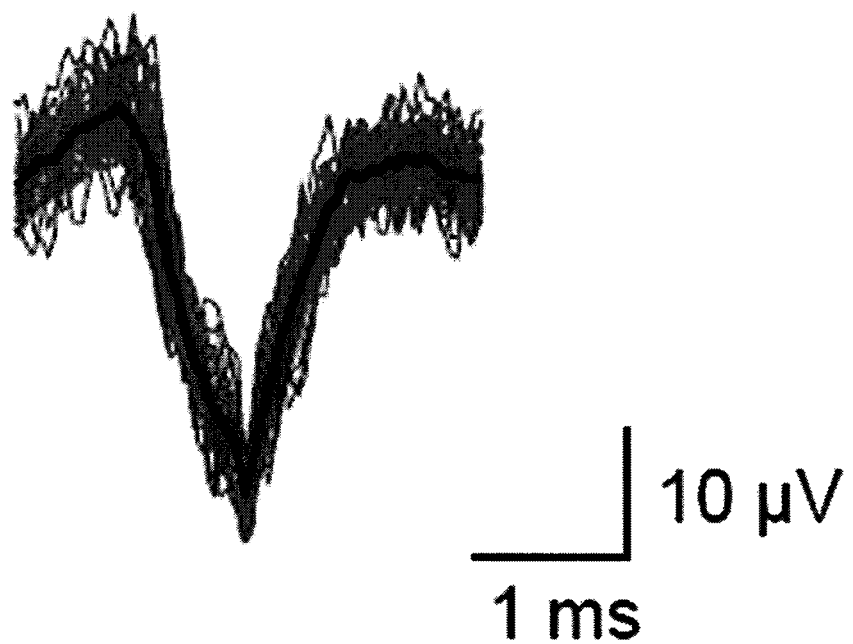

METHOD FOR PRODUCING NERVOUS SYSTEM CELLS

TECHNICAL FIELD

The present invention relates to a method for producing a neural cell from a somatic cell as a material. The present invention also relates to a neural cell obtained by the method, and a composition for treating a nervous system disease, comprising the cell as an effective ingredient.

BACKGROUND ART

Recent development in cell-related study, in particular, many study results relating to pluripotent cells have led to the possibility to obtain therapeutic cells of quality and quantity which allow them to be transplanted to individuals. For some diseases, attempts to transplant cells having effective characteristics for their treatments to patients have been already started.

Regarding nervous system diseases including spinal cord injury, Parkinson's disease, Alzheimer's disease, and amyotrophic lateral sclerosis, possible treatments comprising use of neural cells or neural cell precursors derived from embryo stem cells (ES cells) or induced pluripotent stem cells (iPS cells) have studied.

In regenerative medicine for nervous system diseases, means for obtaining and making therapeutic cells have been needed. Since cells derived from non-self donors and cells differentiated from embryo stem cells are at risk of causing rejection, it is expected that therapeutic cells are obtained by making pluripotent cells (e.g. iPS cells) from autologous cells and then differentiating the pluripotent cells into suitable neural cells. This method requires high conversion efficiency in both a step of making (reprogramming) iPS cells and a step of differentiating the iPS cells into neural cells. In addition, since the method requires a period of several months to obtain neural cells, the method is only applicable to treatments of limited diseases.

On the other hand, a method for directly converting somatic cells such as fibroblasts into neural cells has also been reported. A method comprising gene introduction into somatic cells (Non-patent Literature 1), a method comprising culturing somatic cells with chemical substances, and a method comprising a combination of the above-mentioned methods are known. When a gene is artificially introduced into cells, introduction methods or other conditions may affect the gene expression in the cells. Thus, a method of converting somatic cells into neural cells without performing gene introduction may be more effective.

Thoma et al. have reported that Schwann cells can be obtained by culturing fibroblasts treated with the histone deacetylase inhibitor valproic acid in a medium containing a multikinase inhibitor (compound B), a transforming growth factor (TGF)-β signaling inhibitor, and a glycogen synthase kinase 3β (GSK3β) inhibitor (Non-patent Literature 2). Cheng et al. have reported that neural cell precursors are obtained by culturing fibroblasts in a medium containing valproic acid, a TGF-β signaling inhibitor, and a GSK3β inhibitor, under reduced oxygen conditions (Non-patent Literature 3).

CITATION LIST

Non-Patent Literatures

Non-patent Literature 1: Jikken Igaku (Experimental medicine), 2012, Vol. 30, pp. 189-196

Non-patent Literature 2: Stem Cell Reports, 2014, Vol. 3, pp. 539-547

Non-patent Literature 3: Cell Research, 2014, Vol. 24, pp. 665-679

DISCLOSURE OF INVENTION

Problems to be Solved by the Invention

An object of the present invention is to provide a method of inducing neural cells directly and efficiently from somatic cells in a short time without performing artificial gene introduction.

Solutions to the Problems

The inventors of the present invention intensively studied for a method of obtaining neural cells that could be used in therapy and other uses. As a result, they found that neural cells could be induced from somatic cells with high efficiency by inhibiting Smad signaling and p53 signaling during culture of the somatic cells. Thus, the present invention was completed.

That is, the present invention provides:

[1] a method for producing a neural cell, the method comprising a step of culturing a somatic cell under inhibition of Smad signaling and p53 signaling;

[2] the method according to [1], wherein the Smad signaling is inhibited by a transforming growth factor-β signaling inhibitor or a bone morphogenetic protein signaling inhibitor;

[3] the method according to [1], wherein the p53 signaling is inhibited by a p53 inhibitor;

[4] the method according to [1], wherein the culture of the somatic cell is performed further under a culture condition selected from the group consisting of under inhibition of glycogen synthase kinase 3β signaling, under inhibition of mitogen-activated protein kinase signaling, and a condition that increases the intracellular concentration of cAMP;

[5] the method according to [4], wherein the culture of the somatic cell is performed in a medium containing a transforming growth factor-β signaling inhibitor, a bone morphogenetic protein signaling inhibitor, and a p53 inhibitor, and a substance selected from the group consisting of a glycogen synthase kinase 3β signaling inhibitor, a mitogen-activated protein kinase signaling inhibitor, and an adenylate cyclase activator;

[6] the method according to [1], wherein the culture of the somatic cell is performed further under inhibition of glycogen synthase kinase 3β signaling and mitogen-activated protein kinase signaling, and under a condition increases the intracellular concentration of cAMP;

[7] the method according to [6], wherein the culture of the somatic cell is performed in a medium containing a transforming growth factor-β signaling inhibitor, a bone morphogenetic protein signaling inhibitor, a p53 inhibitor, a glycogen synthase kinase 3β signaling inhibitor, a mitogen-activated protein kinase signaling inhibitor, and an adenylate cyclase activator;

[8] the method according to [1], which does not comprise a step of bringing the somatic cell into contact with a histone deacetylase inhibitor;

[9] the method according to [1], wherein the somatic cell is a differentiated cell;

[10] the method according to [9], wherein the somatic cell is a fibroblast;

[11] the method according to [10], wherein the somatic cell is a human cell;

[12] a neural cell obtained by a method according to any one of claims [1] to [11]; and

[13] a composition for treating a nervous system disease, comprising the cell according to [12] as an effective ingredient.

Effects of the Invention

According to the present invention, neural cells can be directly induced with high efficiency in a short period of time, regardless of the age and background of sources for somatic cells to be used as the material. Moreover, there is no risk of insertion of foreign genes into the cells, and it is possible to acquire safer neural cells.

BRIEF DESCRIPTION OF DRAWINGS

FIG. 1 shows measurement results of action potentials of neural cells obtained by the method of the present invention.

FIG. 2 shows a spike-like waveform extracted from action potential data of neural cells obtained by the method of the present invention.

MODE FOR CARRYING OUT THE INVENTION (1) Neural Cell Production Method of the Present Invention The present invention relates to a neural cell production method comprising a step of culturing a somatic cell under inhibition of Smad signaling and p53 signaling.

The cells of organisms are largely classified into somatic cells and germ cells. In the neural cell production method of the present invention, any somatic cell may be used as a starting material. The somatic cell is not particularly limited, and may be a primary cell taken from a living body or a cell line. In the present invention, somatic cells at various stages of differentiation, for example, terminally differentiated somatic cells, somatic cells on the way to terminal differentiation, and somatic cells that have been reprogrammed and have acquired pluripotency can be used. Examples of the somatic cell that can be used in the present invention include, but not limited to, any somatic cell that does not belong to neural cells, for example, hematopoietic cells (various lymphocytes, macrophages, dendritic cells, bone marrow cells, etc.), organ-derived cells (liver cells, spleen cells, pancreatic cells, kidney cells, lung cells, etc.), muscle tissue cells (skeletal muscle cells, smooth muscle cells, myoblasts, cardiac muscle cells, etc.), fibroblasts, osteoblasts, chondrocytes, endothelial cells, stromal cells, and fat cells. Precursor cells, cancer cells, and various stem cells (hematopoietic stem cells; mesenchymal stem cells, hepatic stem cells, etc.) of the above-mentioned cells can be also used in the method of the present invention.

Examples of sources for the somatic cells include, but not limited to, human and non-human animals. When a neural cell is produced by the method of the present invention for the purpose of administration of the cell to a human, a somatic cell taken out from a donor whose histocompatibility antigen type is same as or similar to that of a recipient is preferably used as the material. More preferably, a somatic cell taken from a recipient is used to induce a neural cell.

Examples of the neural cell obtained by the method of the present invention include, but not limited to, nerve cells (neurons), glial cells (astrocytes, oligodendrocytes, microglia), and Schwann cells. In addition to the above-mentioned terminally differentiated cells, examples of the neural cell in the present invention include various precursor cells destined to differentiate into the above-mentioned terminally differentiated cells.

Smad refers to a group of molecules responsible for intracellular signal transduction of TGF-β superfamily. When Smad is phosphorylated by a receptor bound to a cytokine of TGF-β family, the Smad travels into a nucleus and functions as a transcription activator. Signals transduced by Smad are related to control of cell proliferation, differentiation, and apoptosis.

Means for achieving culture conditions "under inhibition of Smad signaling" in the method of the present invention are not particularly limited. The culture conditions "under inhibition of Smad signaling" can be achieved by known means that can inhibit Smad signaling. In the present invention, a substance that inhibits the function of Smad by directly acting on Smad (e.g. anti-Smad antibodies or other drugs), a drug that inhibits production of Smad, or the like can be utilized. The Smad signaling can be also inhibited by inhibiting upstream of the signal transduction to which Smad contributes. In other words, the present invention can be performed by inhibiting the function of TGF-β family cytokines and/or their receptor. In the method, anti-cytokine antibodies, anti-cytokine receptor antibodies (antagonistic antibodies), cytokine receptor inhibitors and the like can be used. In the present invention, though the present invention is not particularly limited, the Smad signaling is preferably inhibited by inhibiting the signal transduction to which TGF-β and/or bone morphogenetic protein (BMP) contributes by a substance that acts as an inhibitor.

Examples of the TGF-β signaling inhibitor that can be used in the present invention include SB431542 (CAS No. 301836-41-9), RepSox [E-616452] (CAS No. 446859-33-2), A-83-01 (CAS No. 909910-43-6), LY364947 (CAS No. 396129-53-6), and SD208 (CAS No. 627536-09-8). Examples of the BMP signaling inhibitor that can be used in the present invention include LDN-193189 (CAS No. 1062368-24-4), Dorsomorphin (CAS No. 866405-64-3), and Noggin (J Neuroscience, 1995, Vol. 15, p 6077-84). The concentration of the TGF-β signaling inhibitor or the BMP signaling inhibitor which is effective for induction of neural cells may be appropriately determined. Though the present invention is not particularly limited, for example, SB431542 can be used at 0.2 μM to 20 μM and LDN-193189 can be used at 0.1 μM to 10 μM, in the method of the present invention.

Protein p53 is a product of gene p53 known as a tumor suppressor gene, and is involved in cell cycle regulation and apoptosis control. The protein p53 fulfills its function through specific binding to DNA and gene expression control.

Means for achieving culture conditions "under inhibition of p53 signaling" in the present invention are not particularly limited. The culture conditions "under inhibition of p53 signaling" may be achieved by known means that can inhibit p53 signaling. The activity of protein p53 is known to be affected by damage of cells or DNAs. The p53 signaling can be inhibited by subjecting cells to a suitable physical or chemical treatment. Examples of the physical treatment include vibration, irradiation of visible light or radiation, and temperature stimulation. Anti-protein p53 antibodies and known p53 signaling inhibitors are also preferably used in the present invention. Examples of the p53 inhibitor that can be used in the present invention include pifithrin-α (CAS No. 63208-82-2), pifithrin-β (CAS No. 511296-88-1), pifithrin-μ (CAS No. 64984-31-2), NSC66811 (CAS No. 6964-62-1), and Nutlin-3 (CAS No. 548472-68-0). The concentration of the p53 inhibitor which is effective for induction of neural cells may be appropriately determined. Though the present invention is not particularly limited, for example, pifithrin can be used at 0.5 µM to 50 µM in the method of the present invention.

According to the present invention, neural cells can be induced by culturing somatic cells under inhibition of Smad signaling and p53 signaling. The induction efficiency of the neural cells from the somatic cells can be improved by culturing the somatic cells further under inhibition of GSK3β signaling, under inhibition of mitogen-activated protein kinase (MAPK) signaling, or under a condition that increases the intracellular concentration of cAMP, or under any combination of the above-mentioned culture conditions.

GSK3β was found as a protein kinase that phosphorylates and inactivates glycogen synthase. This enzyme has a phosphorylation activity against a variety of proteins, and is involved in not only glycogen metabolism but also cell division, cell proliferation and other physiological phenomena.

Culture conditions "under inhibition of GSK3β signaling" in the method of the present invention are not particularly limited. As a means for inhibiting the GSK3β signaling, a substance that inhibits the activity of GSK3β, for example an anti-GSK3β antibody or a GSK3β inhibitor can be utilized. Since GSK3β loses its activity when a specific site on GSK3β is phosphorylated, a means for promoting the phosphorylation can be also utilized to inhibit the GSK3β signaling. Examples of the GSK3β signaling inhibitor that can be used in the present invention include CHIR99021 (CAS No. 252917-06-9), BIO ((2'Z,3'E)-6-bromoindirubin-3'-oxime; CAS No. 667463-62-9), Kenpaullone (CAS No. 142273-20-9), and A1070722 (CAS No. 1384424-80-9). The concentration of the GSK3β signaling inhibitor which is effective in the method of the present invention may be appropriately determined. Though the present invention is not particularly limited, for example, CHIR99021 can be used at 0.1 µM to 10 µM in the method of the present invention.

MAPK is a protein kinase involved in signal transduction via phosphorylation. MAPK travels into a nucleus when phosphorylated, and then transmit cytoplasmic signals to the nucleus by mainly phosphorylating/activating transcriptional activators.

Culture conditions "under inhibition of MAPK signaling" in the method of the present invention are not particularly limited. As a means for inhibiting the MAPK signaling, a substance that inhibits the activity of MAPK, for example an anti-MAPK antibody or a MAPK inhibitor can be utilized. Means for inhibiting enzymes relating to activation of MAPK, for example MAPK kinase (MAPKK), MAPK kinase kinase (MAPKKK) and the like can be also utilized to inhibit the MAPK signaling. Examples of the MAPK signaling inhibitor that can be used in the present invention include PD0325901 (CAS No. 391210-10-9), PD184352 (CAS No. 212631-79-3), PD98059 (CAS No. 167869-21-8), and PD334581 (CAS No. 548756-68-9). The concentration of the MAPK signaling inhibitor which is effective in the methods of the present invention may be appropriately determined. Though the present invention is not particularly limited, for example, PD0325901 can be used at 0.1 µM to 10 µM in the method of the present invention.

Cyclic adenosine monophosphate (cAMP) is a substance involved in a variety of intracellular signal transduction as a second messenger. In cells, cAMP is produced by cyclization of adenosine triphosphate (ATP) by adenylate cyclase.

Culture conditions "under a condition that increases the intracellular concentration of cAMP" in the method of the present invention are not particularly limited. As a means for increasing the intracellular concentration of cAMP, a substance that can directly act on adenylate cyclase to activate it, a substance capable of promoting the expression of adenylate cyclase, a substance that inhibits phosphodiesterase which is an enzyme that degrades cAMP, or the like can be used. Dibutyryl cAMP which has the same action as cAMP in cells and is a structural analog of cAMP can be also used in the present invention. Examples of the adenylate cyclase activator that can be used in the present invention include forskolin (CAS No. 66575-29-9) and forskolin derivatives (for example, JP-A 2002-348243). The concentration of the adenylate cyclase activator which is effective in the method of the present invention may be appropriately determined. Though the present invention is not limited, for example, forskolin can be used at 0.5 µM to 50 µM in the method of the present invention.

In production of neural cells according to the invention, somatic cells are cultured under conditions that Smad signaling and p53 signaling are inhibited. In addition to the conditions that Smad signaling and p53 signaling are inhibited, a means for inhibiting GSK33 signaling, a means for inhibiting MAPK signaling, or a means for increasing the intracellular cAMP concentration, or any combination of these means may be used.

In a preferable aspect of the present invention, neural cells are induced by culturing somatic cells in a medium containing at least one substance selected from the group consisting of a GSK3β signaling inhibitor, an MAPK signaling inhibitor and an adenylate cyclase activator, in addition to a transforming growth factor-β signaling inhibitor and a bone morphogenetic protein signaling inhibitor as means for inhibiting Smad signaling, and a p53 inhibitor as means for inhibiting p53 signaling. The above-mentioned inhibitors and activator are added to the medium at concentration effective for induction of neural cells. The effective concentration for induction of neural cells may be appropriately determined, and examples thereof include, but not limited to, about 0.1 µM to 50 µM.

In a particularly preferable aspect, neural cells are induced directly from somatic cells by one-step culturing in a medium containing all of a transforming growth factor-β signaling inhibitor, a bone morphogenetic protein signaling inhibitor, a p53 inhibitor, a GSK3β signaling inhibitor, an MAPK signaling inhibitor and an adenylate cyclase activator.

In a preferable aspect of the neural cell production method of the present invention, a histone deacetylase inhibitor is not used in the somatic cell culturing step. In the method of the present invention wherein a histone deacetylase inhibitor which is said to promote reprogramming by nuclear reprogramming factors is not used, there is lower risk of induction of pluripotent cells which may cause unintended differentiation.

The somatic cell culture in the present invention may be performed using a medium, a temperature and other conditions selected depending on the type of the somatic cell while using the above-mentioned means for inhibiting the variety of signaling and the like. The medium can be selected from known media and commercially available media. For example, a medium prepared by adding suitable components (serum, protein, amino acid, sugar, fatty acid, antibiotic, etc.) to general medium MEM, DMEM, or DMEM/F12, or a modified medium can be used.

As the culture conditions, general conditions for cell culture may be selected. For example, the culture conditions include culturing at 37° C. and 5% $CO_2$. It is preferable that the medium is exchanged at appropriate intervals during culture. When the method of the present invention is performed using a fibroblast as the material, a neural cell appears within 10 days to 3 weeks under the above-mentioned conditions. When a somatic cell that can be easily cultured is used, the cell number of the somatic cell can be increased in advance and then converted into neural cells. Thus scaled-up production of neural cells is easily attained.

For the culture, equipment (vessel) for cell culture such as a plate, a dish, a flask for cell culture, or a bag for cell culture can be used. As the bag for cell culture, a bag having gas permeability is preferably used. In a case where a large amount of cells are needed, a large culture tank may be used. The culture can be performed in an open system or a closed system. For the purpose of administration of the neural cells obtained to humans, it is preferable that the culture is performed in a closed system.

(2) Neural Cells Obtained by the Method of the Present Invention

A cell population containing a neural cell can be obtained by the above-mentioned neural cell production method of the present invention.

The induction of neural cells according to the present invention can be confirmed by, for example, morphological changes in cells. Since neural cells have characteristic forms depending on the type of cells, it is possible to know the presence of neural cells by comparing cellular morphology before and after culture. In addition, neural cells can be also confirmed by detecting a molecule (for example, an enzyme, a receptor, a low molecular compound, or the like) characteristic of neural cells. Examples of the molecule characteristic of neural cells include, but not limited to, β3-tubulin, synapsin I, vesicular glutamate transporter (vGULT), microtubule-associated protein (MAP) 2, γ-aminobutyric acid (GABA), and tyrosine hydroxylase. For detection of the molecule, an immunological method (detection with an antibody) can be used. However, for detection of the protein molecule, the mRNA amount of the molecule may be quantified. The antibody that recognizes the molecule characteristic of neural cells is also useful for isolating and purifying the neural cells obtained by the present invention.

The neural cell obtained by the method of the present invention and a composition containing the cell are useful in the treatment of nervous system diseases. Examples of nervous system diseases which the neural cell and the composition is useful for treating include, but not limited to, spinal cord injury, cerebrovascular disorders (cerebral infarction, etc.), Parkinson's disease, Alzheimer's disease, and amyotrophic lateral sclerosis. The neural cell can be also used to produce pharmaceutical compositions for treating the nervous system diseases.

In a case where the neural cell of the present invention is formulated into a pharmaceutical composition, the cell may be formulated into a form suitable for administration to individuals by a conventional method, for example by mixing the cell with a pharmaceutically acceptable carrier. Examples of the carrier include physiological saline, and distilled water for injection which has become isotonic by addition of glucose or other auxiliary agents (e.g., D-sorbitol, D-mannitol, sodium chloride, etc.). In addition, the composition may contain a buffer (e.g., a phosphate buffer, a sodium acetate buffer), a soothing agent (e.g., benzalkonium chloride, procaine hydrochloride, etc.), a stabilizer (e.g., human serum albumin, polyethylene glycol, etc.), a preservative, an antioxidant, and the like.

The neural cell obtained by the present invention can be also used in investigation, for example investigation regarding neural cell differentiation, drug screening for nervous system diseases, evaluation of the efficacy and safety of drug candidate compounds, and the like. According to the present invention, many neural cells can be obtained by a single operation, and therefore it is possible to obtain reproducible results of the investigation without being affected by differences in lots.

EXAMPLES

Hereinafter, the present invention is explained in detail by way of Examples which the present invention is not limited to.

Example 1

Direct Induction of Neural Cells from Human Fibroblasts (1)

1) Human Fibroblasts

Human fibroblasts used as the material were purchased from DS Pharma Biomedical Corporation. Background information about the four cells used is shown in Table 1.

TABLE 1

| Cell | Year old | Gender | Site | BMI |
|---|---|---|---|---|
| 1 | 0 (6 months) | male | foreskin | unknown |
| 2 | 22 | male | breast | 29 |
| 3 | 42 | female | abdomen | 21.8 |
| 4 | 55 | female | abdomen | 28.3 |

2) Direct Induction of Neural Cells from Human Fibroblasts

The human fibroblasts shown in Table 1 were seeded at each $8\times10^4$ cells on 35 mm dishes, and incubated in a DMEM high glucose culture medium containing 10% FBS, 100 U/mL penicillin and 100 μg/mL streptomycin at 37° C. and 5% $CO_2$ for 2 days. Each type of the cells was cultured at the following passage numbers.

Cell 1: Passage 5 (P5) and P20
Cell 2: P5 and P21
Cell 3: P5 and P17
Cell 4: P5 and P15

A neural cell medium containing two compounds for inhibiting Smad signaling, namely LDN-193189 (manufactured by Wako Pure Chemical Industries, Ltd.: final concentration 1 μM) as a BMP signaling inhibitor and SB-431542 (manufactured by Tocris: final concentration 2 μM) as a TGF-β family inhibitor, and CHIR99021 (manufactured by Wako Pure Chemical Industries, Ltd.: final concentration 1 μM) as a GSK3β inhibitor, PD0325901 (manufactured by Wako Pure Chemical Industries, Ltd.: final concentration 1 μM) as a MEK/ERK inhibitor, pifithrin-α (manufactured by Wako Pure Chemical Industries, Ltd.: final concentration 5 μM) as p53 signaling inhibitor, and forskolin (manufactured by Wako Pure Chemical Industries, Ltd.: final concentration 7.5 μM) as a cAMP production promoter was prepared. The neural cell medium was a 1:1 mixture of DMEM/F12 containing 1% (v/v) N2 supplement (manufactured by Lifetech Co., Ltd.), and Neurobasal Medium (manufactured by Lifetech Co., Ltd.) containing 2% (v/v) B27 supplement (manufactured by Lifetech Co., Ltd.). The medium in the dishes containing the human fibroblasts cultured for two days was replaced by the neural cell medium, and then the cell culture was continued at 37° C. and 5% $CO_2$ while the medium was exchanged every 3 days.

3) Evaluation of Neural Cells a) Cell Immunostaining with Neural Cell Markers

After culturing for 3 weeks, the human fibroblasts were morphologically similar to neural cells. The human fibroblasts were fixed with 2% PFA (paraformaldehyde), and then subjected to immunostaining. Antibodies used in the cell immunostaining are mentioned below. For Tuj1, rates of positive cells (neural cells) are shown in Table 2.

Mouse anti-βIII-tubulin [Tuj1] (manufactured by Covance Inc.; MMS-435P)

Rabbit anti-βIII-tubulin [Tuj1] (manufactured by Covance Inc.; PRB-435P)

Rabbit anti-MAP2 (manufactured by Millipore Co., Ltd.)

TABLE 2

| Cell | Passage number | Tuj1 positive cells (%) |
|---|---|---|
| 1 | P5 | 92.4 ± 2.3 |
|   | P20 | 90.5 ± 4.7 |
| 2 | P5 | 87.3 ± 3.5 |
|   | P21 | 89.4 ± 8.1 |
| 3 | P5 | 82.7 ± 5.3 |
|   | P17 | 85.4 ± 4.9 |
| 4 | P5 | 78.6 ± 1.3 |
|   | P15 | 82.1 ± 4.5 |

As shown in Table 2, when the medium containing the six substances was used, cells positive for Tuj1, which is a neural cell marker, appeared at high efficiency exceeding 80% regardless of differences in the sources (ages and genders of the sources, harvest sites of the cells) for the cells used as the material. Further, in any type of the cells, the passage numbers before start of the induction did not affect the induction efficiency. Thus it was shown that the method of the present invention is not affected by cellular aging. Further, in the obtained neural cells, the expression of MAP2, which is a marker of mature neural cells, was confirmed.

From the above results, it was shown that neural cells can be directly induced from fibroblasts by using the above-mentioned six substances for culture.

b) Functional Evaluation of Neural Cells

The cells fixed in the same way as the above a) were subjected to immunostaining using antibodies mentioned below to evaluate the function of neural cells.

Mouse anti-βIII-tubulin [Tuj1] (manufactured by Covance Inc.; MMS-435P)

Rabbit anti-vGLUT1 (manufactured by Synaptic Systems Corp.)

Rabbit anti-GABA (manufactured by Sigma-Aldrich Co., Ltd.)

Rabbit anti-Tyrosine Hydroxylase (manufactured by Millipore Co., Ltd.)

In the obtained neural cells, vGLUT-1, which is a glutamatergic marker, was expressed and the presence of γ-aminobutyric acid (GABA), which is an inhibitory neurotransmitter marker, was confirmed, but the expression of tyrosine hydroxylase, which is a dopaminergic marker, was not confirmed. Therefore, the neural cells produced by the present invention are probably both glutamatergic neural cells and inhibitory neural cells.

Example 2

Direct Induction of Neural Cells from Human Fibroblasts (2)

The neural cell medium containing the six substances used in Example 1, and the same neural cell media lacking any one of the six substances were used to perform direct induction of neural cells from fibroblasts. As a control, the cell culture was performed using the neural cell medium lacking all of the six substances.

Using each of the above-mentioned media, Cell 2 (P5) described in Example 1 was cultured as described in Example 1. After culturing for 2 weeks, the cells were fixed with 2% PFA and then subjected to immunostaining using the mouse anti-βIII-tubulin. Results are shown in Table 3. In the table, the description "6c—[Compound Name]" indicates use of a medium lacking the indicated compound as compared with the neural cell medium containing the six substances.

TABLE 3

| Medium | Tuj1 positive cells (%) |
|---|---|
| 6c | 57.3 ± 3.5 |
| control | 0 |
| 6c - pifithrin-α | 0 |
| 6c - forskolin | 13.8 ± 2.2 |
| 6c - CHIR99021 | 24.6 ± 4.8 |
| 6c - PD0325901 | 15.2 ± 3.5 |
| 6c - LDN-193189 | 11.3 ± 1.4 |
| 6c - SB-431542 | 15.1 ± 1.8 |

As shown in Table 3, when the medium containing the six substances was used, the neural cells were induced with high efficiency. When the medium lacking pifithrin-α and the medium not containing all of the six substances were used, the neural cells did not appear. However, when the other media were used, the induction of neural cells was confirmed. Thus, it was found that inhibiting p53 signaling is probably essential for the induction of neural cells from fibroblasts.

Further, when the cell culture was performed in the neural cell medium lacking two substances LDN-193189 and SB-431542, i.e., in the absence of means for inhibiting Smad signaling, the induction of neural cells was not observed.

From the above results, it was shown that inhibiting two pathways of p53 signaling and Smad signaling during culture is essential for the direct induction of neural cells from fibroblasts.

Example 3

Direct Induction of Neural Cells from Human Fibroblasts (3)

Cell 2 (P5) described in Example 1 was cultured in the neuronal cell medium containing the six substances described in Example 1 under the same conditions as in Example 1. After culturing for 1 week, 2 weeks, 3 weeks and 4 weeks, a part of the cells were collected, fixed with 2% PFA, and then subjected to immunostaining using the mouse anti-βIII-tubulin. Cells positive for Tuj1 were quantified. Results are shown in Table 4.

TABLE 4

| Culture period | Tuj1 positive cells (%) |
|---|---|
| 1 week | 8.4 ± 2.7 |
| 2 weeks | 58.5 ± 4.1 |
| 3 weeks | 88.2 ± 3.9 |
| 4 weeks | 89.2 ± 2.1 |

As shown in Table 4, when the medium containing the six substances was used, the proportion of neural cells exceeded 50% after 2 weeks from the start of the culture. Moreover, it was shown that the induction of neural cells reached the maximum value after culturing for about 3 weeks.

Example 4

Measurement of Action Potential

1) Induction of Neural Cells

Neural cells were induced from human fibroblasts (derived from 48 year-old female skin/labia) in the same way as Example 1. After culturing for 4 weeks, the induced neural cells were detached using 0.25% trypsin (manufactured by Wako Pure Chemical Industries), and suspended in a neural cell medium [a 1:1 mixture of DMEM/F12 containing 1% (v/v) N2 supplement (manufactured by Lifetech Co., Ltd.), and Neurobasal Medium (manufactured by Lifetech Co., Ltd.) containing 2% (v/v) B27 supplement (manufactured by Lifetech Co., Ltd.)].

2) Measurement of Action Potential

For measurement of the action potential of the neural cells, a microelectrode array system (MED64-Basic system; manufactured by the Alpha Med Scientific, Inc.) was used. Prior to use, the surface of an MED probe with an electrode was coated with collagen. First, a 10-fold diluted solution of collagen (cell matrix Type I-C; manufactured by Nitta Gelatin Inc.) was prepared using the neural cell medium. The collagen solution was added to the MED probe. After the MED probe was left for 10 minutes, the collagen solution was removed from the probe. The probe was air-dried under ultraviolet irradiation in a clean bench.

After the MED probe coated with collagen was washed 3 times with sterile water, the suspension of neural cells obtained in Example 4-1) was added to the probe and cultured in the medium used in Example 4-1) at 37° C. for 7 days. Then, the probe was connected to the microelectrode array system to measure action potential. An example of a waveform obtained by serial measurement of action potential is shown in FIG. 1. In FIG. 1, the horizontal axis represents elapsed time, and the vertical axis represents voltage. FIG. 2 shows a spike-like waveform extracted from the data of the action potential. In this figure, 20 waveforms are superposed, and a waveform obtained by averaging the 20 waveforms is shown by a solid line. Thus, it was found that the neural cells obtained by the method of the present invention generate action potential.

Example 5

Direct Induction of Neural Cells from Human Fibroblasts (4)

To the neural cell medium containing the 6 substances used in Example 1, Dorsomorphin (a BMP signaling inhibitor; manufactured by Wako Pure Chemical Industries, Ltd.) was further added at a final concentration of 5 µM. The neural cell medium thus prepared was used to perform direct induction of neural cells from fibroblasts.

Human fibroblasts were pre-cultured in a DMEM high glucose medium containing 10% FBS, 100 U/mL penicillin and 100 µg/mL streptomycin in the same way as Example 1. Then, the medium was replaced by the neural cell medium, and the cell culture was continued at 37° C. and 5% $CO_2$ while the medium was exchanged every 3 days. After culturing for 11 days, the cells were subjected to immunostaining with the anti-Tuj1 antibody, the anti-MAP2 antibody, and an anti-SnynapsinI antibody (manufactured by Millipore). As a result, it was shown that neural cells positive for these markers were obtained. Further, almost the same result was obtained when the final concentration of Dorsomorphin in the neural cell medium was changed to 1 µM or 10 µM and the cell culture was performed.

Thus, it was shown that neural cells can be induced even when the BMP signaling is inhibited by plural compounds. Further, the combined use of Dorsomorphin shortened the time to the appearance of neural cells.

INDUSTRIAL APPLICABILITY

The present invention provides a method of directly inducing neural cells with high efficiency and in a short time. The method of the present invention is not affected by the nature and background of a somatic cell used as a material, and is easily scaled up. Therefore, the method of the present invention enables stable supply of neural cells. The neural cells obtained by the method of the present invention are useful in the fields of various studies and medicine.

The invention claimed is:

1. A method for producing a neural cell, the method comprising a step of culturing a somatic cell under inhibition of Smad signaling and p53 signaling,
    wherein the Smad signaling is inhibited by a transforming growth factor-β signaling inhibitor or a bone morphogenetic protein signaling inhibitor and the p53 signaling is inhibited by a p53 inhibitor,
    wherein the neural cell is produced directly from the somatic cell without undergoing induction of a pluripotent stem cell,
    wherein the method does not comprise a step of bringing the somatic cell into contact with a histone deacetylase inhibitor,
    wherein the method does not comprise artificial gene introduction, and
    wherein the somatic cell is a differentiated somatic cell.

2. The method according to claim 1, wherein the culture of the somatic cell is performed further under a culture condition selected from the group consisting of under inhibition of glycogen synthase kinase 3β signaling, under inhibition of mitogen-activated protein kinase signaling, and a condition that increases the intracellular concentration of cAMP.

3. The method according to claim 2, wherein the culture of the somatic cell is performed in a medium containing a transforming growth factor-β signaling inhibitor, a bone morphogenetic protein signaling inhibitor, and a p53 inhibitor, and a substance selected from the group consisting of a glycogen synthase kinase 3β signaling inhibitor, a mitogen-activated protein kinase signaling inhibitor, and an adenylate cyclase activator.

4. The method according to claim 1, wherein the culture of the somatic cell is performed further under inhibition of glycogen synthase kinase 3β signaling and mitogen-activated protein kinase signaling, and under a condition that increases the intracellular concentration of cAMP.

5. The method according to claim 4, wherein the culture of the somatic cell is performed in a medium containing a transforming growth factor-β signaling inhibitor, a bone morphogenetic protein signaling inhibitor, a p53 inhibitor, a glycogen synthase kinase 3β signaling inhibitor, a mitogen-activated protein kinase signaling inhibitor, and an adenylate cyclase activator.

6. The method according to claim 1, wherein the somatic cell is a fibroblast.

7. The method according to claim 6, wherein the somatic cell is a human cell.

* * * * *